(12) United States Patent
Bellemore et al.

(10) Patent No.: US 10,918,664 B2
(45) Date of Patent: *Feb. 16, 2021

(54) CHEWABLE EYE HEALTH FORMULATION

(71) Applicants: Marc Bellemore, Windsor (CA); Ashley V Kasurak, Windsor (CA); Paul Charlton, Windsor (CA); Megan Thomas, Windsor (CA); John Doherty, Windsor (CA); Sorin Popa, Windsor (CA)

(72) Inventors: Marc Bellemore, Windsor (CA); Ashley V Kasurak, Windsor (CA); Paul Charlton, Windsor (CA); Megan Thomas, Windsor (CA); John Doherty, Windsor (CA); Sorin Popa, Windsor (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/942,327

(22) Filed: Mar. 30, 2018

(65) Prior Publication Data

US 2018/0221408 A1 Aug. 9, 2018

Related U.S. Application Data

(63) Continuation of application No. 14/829,728, filed on Aug. 19, 2015, now Pat. No. 9,950,008.

(60) Provisional application No. 62/039,852, filed on Aug. 20, 2014.

(51) Int. Cl.
| | |
|---|---|
| *A61K 33/30* | (2006.01) |
| *A61K 33/34* | (2006.01) |
| *A61K 31/375* | (2006.01) |
| *A61K 31/355* | (2006.01) |
| *A61K 31/047* | (2006.01) |
| *A61K 9/00* | (2006.01) |
| *A61K 36/45* | (2006.01) |
| *A61K 36/28* | (2006.01) |

(52) U.S. Cl.
CPC ............ *A61K 33/30* (2013.01); *A61K 9/0056* (2013.01); *A61K 31/047* (2013.01); *A61K 31/355* (2013.01); *A61K 31/375* (2013.01); *A61K 33/34* (2013.01); *A61K 36/28* (2013.01); *A61K 36/45* (2013.01)

(58) Field of Classification Search
CPC ........ A61K 33/30; A61K 36/28; A61K 36/45; A61K 9/0056; A61K 33/34; A61K 31/047; A61K 31/355; A61K 31/375
See application file for complete search history.

(56) References Cited

U.S. PATENT DOCUMENTS

| 8,183,227 B1 * | 5/2012 | Perrin | A23L 33/12 514/52 |
|---|---|---|---|
| 2005/0032914 A1 * | 2/2005 | Barker | A61K 31/07 514/763 |
| 2007/0141170 A1 * | 6/2007 | Lang | A61K 31/015 424/638 |
| 2007/0265351 A1 * | 11/2007 | Kumar | A61K 31/045 514/725 |
| 2013/0243845 A1 * | 9/2013 | Geron | A23G 1/42 424/440 |

FOREIGN PATENT DOCUMENTS

WO WO2012/019010 A2 * 2/2012

OTHER PUBLICATIONS

Food and Drug Administration's "Quality Attribute Considerations for Chewable Tablets—Guidance for Industry" dated Aug. 2018.
AREDS2 Research Group (2013) Journal of the American Medical Association vol. 309, pp. 2005-2015 "Lutein + Zeaxanthin and Omega-3 Fatty Acids for Age-Related Macular Degeneration: The Age-Related Eye Disease Study 2 (AREDS2) Randomized Clinical Trial".
AREDS Research Group (2000) Journal of Nutrition vol. 130, pp. 1516S-1519S "The Age-Related Eye Disease Study: A Clinical Trial of Zinc and Antioxidants—Age-Related Eye Disease Study Report No. 2".
AREDS Research Group (2001) Arch Ophthalmol. vol. 119, pp. 1417-1436 "A Randomized, Placebo-Controlled, Clinical Trial of High-Dose Supplementation With Vitamins C and E, Beta Carotene, and Zinc for Age-Related Macular Degeneration and Vision Loss—AREDS Report No. 8".
AREDS Research Group (2004) Arch Ophthalmol. vol. 122, pp. 716-726 "Associations of Mortality With Ocular Disorders and an Intervention of High-Dose Antioxidants and Zinc in the Age-Related Eye Disease Study: AREDS Report No. 13".

* cited by examiner

*Primary Examiner* — Aradhana Sasan
*Assistant Examiner* — Quanglong N Truong

(57) ABSTRACT

Risk of visual impairment including Age-Related Macular Degeneration (AMD) and cataracts increase with age. This increased risk can be caused by changes in the structure and function of the eye or changes in structures of the central nervous system that support visual perception. The present invention comprises fruit flavored, chewable formulations of supplements for reducing the risk of AMD. Chewable dosage forms of the invention are preferred over other formulations and may increase compliance in an aging population, who are more likely to require an eye health supplement and have an increased risk of experiencing dysphagia.

6 Claims, No Drawings

CHEWABLE EYE HEALTH FORMULATION

BACKGROUND OF THE INVENTION

Risk of visual impairment which includes Age-Related Macular Degeneration (AMD) and cataracts increases as the average person ages. This can be due to changes in the structure and function of the eye itself as well as changes that can affect the functionality of the structures in the central nervous system that support visual perception. Dagnelie G. (2013). Age-related psychophysical changes and low vision. Invest Ophthalmol Vis Sci, 54(14): ORSF88-93.

The Age Related Eye Disease Study (AREDS) is a long-term multicenter study that has investigated the natural progression of AMD and its improvement with supplementation. The AREDS study group tested variations of formulations and determined the most effective formulation to contain lutein, zeaxanthin, copper, zinc, vitamin C, and vitamin E. A variety of zinc levels did not alter the effectiveness. Prior to the present invention, the AREDS studies, and supplements arising therefrom, were done using supplementation that required the participant to swallow an oral dosage form. However, the population that would benefit the most from an eye health related supplement would also be at a higher risk of dysphagia, which is a common issue as people age.

Two of the more severe visual impairments that can occur are Age-Related Macular Degeneration (AMD) and cataracts. AMD is an incurable disease characterized by drusen, retinal pigment epithelial abnormalities, geographic atrophy, retinal pigment epithelial detachment, choroidal neovascularization and disciform scarring. Age-Related Eye Disease Study Research Group. (1999). The Age-Related Eye Disease Study (AREDS): Design Implications AREDS Report No. 1. *Control Clin Trials,* 20(6): 573-600.

AMD is the leading cause of blindness in the developed world and the number of people with advanced AMD is expected to double over the next twenty (20) years, while cataracts are opacities in a lens which is normally transparent. The most common type of cataract is age-related and is the leading cause of visual impairment and blindness in the United States of America (USA).

In 1999, the Age-Related Eye Disease Study (AREDS) was conceived as a long-term multicenter study of the natural progression of AMD. The study spanned eleven (11) clinical centers across the USA and was sponsored by the National Eye Institute. The AREDS study included a randomized clinical trial involving 4757 participants aged 55-80 years, which was designed to evaluate the effect of a high dose supplement of antioxidant vitamins and minerals on the progression of AMD and cataract. At the time of the first AREDS study, there was an absence of clinical studies with definitive results on the safety and efficacy of pharmacologic doses of vitamins and minerals to treat these two particular eye conditions. Due to extensive marketing, the general public, however, still sought these formulations in order to self-medicate their conditions. Therefore, the AREDS study was conducted to provide descriptive data on the clinical course of AMD and cataract, attempt to identify factors that influence their development and progression, as well as evaluate the potential efficacy of an antioxidant rich vitamin and mineral formulation.

The formulation evaluated by the AREDS researchers contained five hundred (500) mg of vitamin C, four hundred (400) international units (IU) of vitamin E, fifteen (15) mg of beta-carotene, eighty (80) mg of zinc, and two (2) mg of copper; copper was added to the formulations containing zinc to prevent deficiency. The chosen formulation was based on recommendations from expert nutritionists, ophthalmologists and biochemists who reviewed existing science and epidemiological data. The benefits of supplementation with this combination of vitamins and minerals was observed in people who began the study at high risk for developing advanced AMD, those with intermediate AMD, and those with advanced AMD in one eye only. Those taking the supplement for five years had a reduced risk of developing advanced stages of AMD and its accompanying visual loss over the supplementation period by twenty-five (25) percent. This was the first clinical study to examine people at high risk for developing advanced AMD. The first AREDS study showed that slowing the progression of AMD could save the vision of those at risk of impairment. Age-Related Eye Disease Study Research Group. (2001). A Randomized, Placebo-Controlled, Clinical Trial of High-Dose Supplementation With Vitamins C and E, Beta Carotene, and Zinc for Age-Related Macular Degeneration and Vision Loss: AREDS Report No. 8. *Arch Ophthalmol,* 119: 1417-36.

The Age-Related Eye Disease Study 2 (AREDS2) was conducted to assess whether the formulation could be improved upon by adding omega-3 fatty acids, lutein and zeaxanthin, as well as removing beta-carotene and/or reducing zinc. Observational studies have suggested that omega-3 fatty acids along with the carotenoids lutein and zeaxanthin may be associated with a decreased risk of developing advanced AMD. The placebo-controlled, randomized, double-blind portion of the AREDS2 study was conducted in 2006-2012 with 4203 participants enrolled who were aged 50-85 years. Participants enrolled in the AREDS2 study were at risk for progression to AMD with bilateral large drusen or a large drusen in one (1) eye and advanced AMD in the other eye. Participants were randomized to receive supplements containing ten (10) mg lutein and two (2) mg zeaxanthin or three hundred and fifty (350) mg DHA and six hundred and fifty (650) mg EPA or ten (10) mg lutein, two (2) mg zeaxanthin, three hundred and fifty (350) mg DHA and six hundred and fifty (650) mg EPA. All participants were also supplemented with the original AREDS formulation or a secondary randomization to variations of the AREDS formulation, including elimination of beta carotene, lowering the amount of zinc, or both. Age-Related Eye Disease Study 2 (AREDS2) Research Group. (2013). Lutein+Zeaxanthin and Omega-3 Fatty Acids for Age-Related Macular Degeneration: The Age-Related Eye Disease Study 2 (AREDS2) Randomized Clinical Trial. *JAMA,* 309 (19): 2005-15.

The modified formulation in the AREDS2 study which contained omega-3 fatty acids or lutein and zeaxathin or both showed no statistically significant difference in risk reduction of AMD over the original AREDS formula. However, the AREDS2 study group did find that individuals low in dietary lutein and zeaxanthin were about 25% less likely to develop advanced AMD compared to participants with similar dietary intake who did not take lutein and zeaxanthin. The removal of beta-carotene did not affect the formulation's protective effect against developing AMD. The researchers found that formulations containing lutein and zeaxanthin and no beta-carotene had a reduction in developing advanced AMD by 18% compared to participants who took the AREDS2 formula with beta-carotene and no lutein or zeaxanthin. Beta-carotene was shown to compete with lutein and zeaxanthin as individuals who took all three nutrients had lower levels of circulating lutein and zeaxanthin when compared to participants who took lutein and zeaxanthin without beta-carotene. The AREDS2 study also showed lowering the amount of zinc had no effect on AMD progression but there was a positive association found between beta-carotene and the risk of lung cancer among former smokers. The AREDS2 clinical trial provides evidence that long-term use of AREDS supplements appears safe and protective against advanced AMD and the addition of lutein and zeaxanthin in place of beta-carotene further improves the original formulation.

U.S. Pat. No. 6,660,297 discloses retinal health supplements containing: approximately 7 to 10 times the RDA of vitamin C; approximately 13 to 18 times the RDA of vitamin E; approximately 6 to 10 times the RDA of vitamin A in the form of beta-carotene; approximately 4 to 7 times the RDA of Zinc; and at least 1.6 mg copper.

U.S. Pat. No. 7,267,830 claims dietary supplements for macular degeneration comprising approximately 0.03% to 0.3% copper (by weight), approximately 0.2% to 4% zinc (by weight), approximately 10% to 30% Vitamin C (by weight), and approximately 1.0% to 25% co-beadlets (by weight), wherein the co-beadlets comprise: approximately 0.5% to 25% Vitamin E (by weight), and approximately 10% to 30% (by weight) active carotenoid in the form of β-carotene and xanthophyll selected from the group consisting of lutein, zeaxanthin, and a mixture thereof. It also claims: dietary supplements further comprising: about 125 mg Vitamin C; about 0.4 mg copper; about 20 mg Zinc; and said co-beadlets, which comprise: about 100 IU Vitamin E about 0.75 mg [3-carotene; about 11.25 mg lutein; and about 3.75 mg Zeaxanthin.

Age-Related Eye Disease Study Research Group. (2000). The Age-Related Eye Disease Study: A Clinical Trial of Zinc and Antioxidant—Age-Related Eye Disease Study Report No. 2. *J Nutr,* 130(5S): 1516S-19S.

Seddon J M, et al. (1994). Dietary carotenoids, vitamins A, C, and E and advanced age-related macular degeneration. *JAMA,* 272(18): 1413-20.

SanGiovanni J P, et al. Age-Related Eye Disease Study Research Group. (2007). The relationship of dietary carotenoid and vitamin A, E and C intake with age-related macular degeneration in a case-control study: AREDS Report No. 22. Arch Ophthalmol, 125: 1225-32.

Augood C, et al. (2008). Oily fish consumption, dietary docosahexaenoic acid and eicosapentaenoic acid intakes, and associations with neovascular age-related macular degeneration. Am J Clin Nutr, 88(2): 398-406.

Aslam M & Vaezi M F. (2013). Dysphagia in the Elderly. Gastroenterol Hespatol, 9(12): 784-95.

DETAILED DESCRIPTION OF THE INVENTION

We presented participants with two chewable forms of the AREDS formulation which had differing levels of zinc. As we expected, there was no difference in preference between the two tablets for color/appearance. The chewable tablet with the lowered level of zinc achieved superior results for texture/mouthfeel, bitterness, sweetness, aftertaste, odor/aroma and overall taste/flavor. Overall, a chewable dosage format may increase compliance in an aging population, who are more likely to require an eye health supplement and have an increased risk of experiencing dysphagia.

The formulations studied were the AREDS 2 formula without beta-carotene and a modified/novel AREDS 2 formula according to the invention that is without beta-carotene and comprises a reduced amount of zinc. The AREDS 2 formula, which contains no beta-carotene, was selected due to the interaction the AREDS research group had previously observed between beta-carotene and lutein and zeaxanthin. The novel version of the AREDS 2 formula according to the present invention was developed with the hope that less zinc in a chewable dosage form would improve texture/mouthfeel and aftertaste of the formulation. There are currently no chewable AREDS formulations on the market, a delivery form which would be beneficial for the targeted aging population, who often have troubles with dysphagia. The current double-blinded, randomized, positive control trial was designed to compare two AREDS formulations in a chewable delivery form for sensory analysis to determine optimal taste for a chewable antioxidant rich vitamin and mineral blend.

In conclusion, the current double-blind, randomized, positive controlled trial observed that the modified/novel AREDS formulation according to the invention with no beta-carotene and a reduced amount of zinc was preferred over the original formulation in a chewable delivery format. There was a significant percentage of individuals who preferred the tablet with the reduced amount of zinc (12.5 mg, Sample A) compared to those who preferred the original AREDS 2 formulation, which contained forty milligrams (40 mg, Sample B) of zinc.

The AREDS 2 chewable tablet according to the present invention was preferred over the AREDS 2 chewable tablet with no beta-carotene for overall taste/flavor, odor/aroma, texture/mouthfeel, bitterness, sweetness and aftertaste. The only criteria that was evaluated by the sample population that did not have a preference towards sample A (the inventive formulation) was color/appearance for which no preference for either tablet was shown. This finding was expected as the tablets were formulated to look identical.

Overall, the chewable dosage forms of the invention may increase compliance for the aging population, who are more likely to require an eye health supplement and have an increased probability of experiencing dysphagia. As noted by the AREDS research group, the formulation containing lutein and zeaxanthin with no beta-carotene was proven to be more efficacious compared to the original AREDS formulation that included beta-carotene.

In addition, a reduction in the amount of zinc did not reduce the overall efficacy of the original formula. The reduction in zinc in the novel/modified formula from 40 mg to 12.5 mgs will also help to increase compliance due to the overall improvement in taste/aroma, texture/mouthfeel, sweetness and a reduction in aftertaste.

Further, as disclosed in the examples below, while the invention may also be made with other flavorings, natural and/or artificial, the preferred embodiments are natural fruit flavored chewable dosage forms of the invention, such as those comprising strawberry, raspberry, or blueberry flavors. Other flavors that may be used in the present invention include, but are not limited to, mint, chocolate, vanilla, butterscotch, anise or licorice, cinnamon, honey, coffee, nut flavored, banana, grape, orange, cherry, mango, peach, pear, apricot, watermelon, melon, apple, kiwi, passionfruit, pomegranate, lemon, lime, grapefruit.

Examples of embodiments of the invention are provided of the invention in detail below. It is to be understood that the invention is not limited in its application to the details of set forth in the following. The invention is capable of other embodiments and of being practiced and carried out in various ways as described herein. Also, it is to be understood that the phraseology and terminology employed herein are for the purpose of the description and should not be regarded as limiting.

EXAMPLES

Example 1

Two test formulas were prepared for evaluation. 1—A chewable tablet based on the AREDS 2 formula and 2—a novel AREDS formula with a revised level of zinc for improved palatability. Both tablets were identical in size, color and shape.

TABLE 1

| AREDS 2 Formula | NOVEL AREDS Formula |
|---|---|
| Vitamin C (ascorbic acid, sodium ascorbate) 250 mg | Vitamin C (ascorbic acid, sodium ascorbate) 250 mg |
| Vitamin E (d-alpha tocopheryl acetate) 134 mg | Vitamin E (d-alpha tocopheryl acetate) 134 mg |
| Zinc (zinc oxide) 40 mg | Zinc (zinc oxide) 12.5 mg |
| Copper (copper citrate) 1.0 mg | Copper (copper citrate) 0.5 mg |
| Lutein (*Tagetes erecta*, marigold flower) 5 mg | Lutein (*Tagetes erecta*, marigold flower) 5 mg |
| Zeaxanthin (*Tagetes erecta*, marigold flower, ketoisophorone) 1 mg | Zeaxanthin (*Tagetes erecta*, marigold flower, ketoisophorone) 1 mg |

A sample size of 50 healthy individuals was estimated to be a sufficient representation of the general population. Individuals were excluded if there was any concern of interaction with current medications, pregnancy, or illness. Researchers administrating the test were blinded to which formula was allocated as sample A and sample B.

Study Design

Each individual was asked to have a drink of water and eat a soda cracker to cleanse their palate; an uncleansed palate may interfere with the tasting process. They were then asked to taste the first sample (sample A). Following the first sample, individuals were asked to have another drink of water and a soda cracker to cleanse their palates again, removing the remaining taste from the first sample. Once their palates had been cleansed they were asked to taste the second sample and complete a questionnaire, where they were then required to indicate their overall preference. Samples were evaluated on seven (7) criteria: Color/Appearance, Overall Taste/Flavor, Odour/Aroma, Texture/Mouthfeel, Bitterness, Sweetness, and Aftertaste.

Data Analysis

Researchers were unblinded only after all results had been tallied. The overall preference for each variable was determined by the majority of individuals that selected a sample. The number of participants that selected an overall tablet preference was also tallied.

Results

Sixty (60) individuals were recruited to evaluate the samples; forty-five (45) individuals completed the evaluation. Two (2) individuals withdrew from the evaluation due to medical concerns and thirteen (13) withdrew for various reasons including illness (ex. cold/flu).

Sample A was the Novel AREDS formulation and sample B was the AREDS 2 formulation. The tallied results from the survey of forty-five (45) individuals are listed below in Table 2. Each number in the Table represents one (1) individual that preferred either sample A or sample B; the researchers also included no preference in Table 2 after completed evaluation sheets indicated that some individuals did not have a preference for one or more criteria.

Sample A was preferred for all criteria (Overall Taste/Flavor, Odour/Aroma, Texture/Mouthfeel, Bitterness, Sweetness, and Aftertaste) except color/appearance for which the majority of individuals had no preference. Overall, a significant number of individuals preferred sample A [twenty-eight (28) of forty-five (45); sixty-two percent (62%)].

TABLE 2

Results from the taste test were tallied based on the number of individuals that selected a preference for one sample over the other for each of the seven (7) criteria. No preference was indicated on evaluation sheets by either both samples or no sample being selected. Sample A was the Novel AREDS formulation and sample B was the Original AREDS formulation.

Sample Preference

| Criteria | A | B | No Preference | Preference |
|---|---|---|---|---|
| Color/Appearance | 13 | 13 | 19 | None |
| Overall Taste/Flavor | 28 | 15 | 2 | A |
| Odour/Aroma | 16 | 14 | 15 | A |
| Texture/Mouthfeel | 29 | 11 | 6 | A |
| Bitterness | 23 | 15 | 7 | A |
| Sweetness | 21 | 19 | 5 | A |
| Aftertaste | 27 | 11 | 5 | A |
| Overall Preference: | 28 | 17 | 0 | A |

Results from the taste test were tallied based on the number of individuals that selected a preference for one sample over the other for each of the seven (7) criteria. No preference was indicated on evaluation sheets by either both samples or no sample being selected. Sample A was the Novel AREDS formulation and sample B was the Original AREDS formulation.

Example 2

Natural Fruit Flavor Formulas

TABLE 3

| Active | Raw Material | Active Amount per | Raw per tablet | Units | % tablet |
|---|---|---|---|---|---|
| Cantab+ | | 34.5 | 34.5000 | mg | 1.5000 |
| Zinc | Oxide | 12.5 | 32.0513 | mg | 1.3935 |
| Copper | Citrate | 0.5 | 1.3889 | mg | 0.0604 |
| Sucralose | | 2.3 | 2.3000 | mg | 0.1000 |
| Vit E | Acetate | 200 | 234.0426 | IU | 10.1758 |
| Lutein | | 5 | 125.0000 | mg | 5.43 |
| Zeaxanthin | | 0.75 | 18.7500 | mg | 0.82 |
| Vit C | Ascorbic Acid | 120 | 132.6316 | mg | 5.77 |
| Vit C | Na Ascorbate | 130 | 156.7164 | mg | 6.81 |
| Citric acid | | 10 | 10.0000 | mg | 0.43 |
| Blueberry | Flv | 9.45 | 9.4500 | mg | 0.41 |
| Strawberry | Flv | 10.505 | 10.5050 | mg | 0.46 |
| Raspberry | Flv | 10.505 | 10.5050 | mg | 0.46 |
| Bilberry | | 46 | 46.0000 | mg | 2.00 |

Example 3

Natural Flavors Improve Sensory Perception of Novel Eye Health Formulation

Methods/Materials

Two test formulas were prepared for this evaluation. 1—A novel chewable tablet based on the AREDS formula with a revised level of zinc for improved palatability which included natural flavors and 2—a novel AREDS formula with a revised level of zinc for improved palatability which did not include any added flavors. Both tablets were

TABLE 4

| NOVEL AREDS Formula With Added Flavors | NOVEL AREDS Formula Without Added Flavors |
|---|---|
| Vitamin C (ascorbic acid, sodium ascorbate) 250 mg | Vitamin C (ascorbic acid, sodium ascorbate) 250 mg |
| Vitamin E (d-alpha tocopheryl acetate) 134 mg AT/200 IU | Vitamin E (d-alpha tocopheryl acetate) 134 mg AT/200 IU |
| Zinc (zinc oxide) 12.5 mg | Zinc (zinc oxide) 12.5 mg |
| Copper (copper citrate) 0.5 mg | Copper (copper citrate) 0.5 mg |
| Lutein (*Tagetes erecta*, marigold flower) 5 mg | Lutein (*Tagetes erecta*, marigold flower) 5 mg |
| Zeaxanthin (*Tagetes erecta*, marigold flower, ketoisophorone) 1 mg | Zeaxanthin (*Tagetes erecta*, marigold flower, ketoisophorone) 1 mg |
| Excipients include Bilberry Fruit Extract. | Excipients include Bilberry Fruit Extract. |

A sample size of ten (10) healthy individuals was estimated to be a sufficient representation of the general population. Individuals were excluded if there was any concern of interaction with current medications, pregnancy, or illness. Researchers administering the test were blinded to which formula was allocated as sample A and sample B.

Study Design

Each individual was asked to have a drink of water and eat a soda cracker to cleanse their palate; an uncleansed palate may interfere with the tasting process. They were then asked to taste the first sample (sample A). Following the first sample, individuals were asked to have another drink of water and a soda cracker to cleanse their palates again, removing the remaining taste from the first sample. Once their palates had been cleansed they were asked to taste the second sample and complete the questionnaire, where they were then required to indicate their overall preference. Samples were evaluated on seven (7) criteria: Color/Appearance, Overall Taste/Flavor, Odour/Aroma, Texture/Mouthfeel, Bitterness, Sweetness, and Aftertaste.

Data Analysis and Recommendations

Researchers were unblinded only after all results had been tallied. The overall preference for each variable was determined by the majority of individuals that selected a sample. The number of participants that selected an overall tablet preference was also tallied.

Results

Sixteen (16) individuals were recruited to evaluate the samples; all individuals completed the evaluation.

Sample A was the Novel AREDS formulation without any added flavors and sample B was the Novel AREDS formulation with added natural flavors. The tallied results from the survey of sixteen (16) individuals are listed below in Table 5. Each number in the Table represents one (1) individual that preferred either sample A or sample B; the researchers also included no preference in Table 5 after completed evaluation sheets indicated that some individuals did not have a preference for one or more criteria.

Sample B was preferred for all criteria (Color/Appearance, Overall Taste/Flavor, Odour/Aroma, Texture/Mouthfeel, Bitterness, Sweetness, and Aftertaste). Overall, a highly significant number of individuals preferred sample B [sixteen (16) of sixteen (16); one hundred percent (100%)]. It is worth noting that there was a non-significant difference in the color/appearance of the two tablets, as they were formulated to look the same.

Results from the taste test were tallied based on the number of individuals that selected a preference for one sample over the other for each of the seven (7) criteria. No preference was indicated on evaluation sheets by either both samples or no sample being selected. Sample A was the Novel AREDS formulation with no added flavor and sample B was the Novel AREDS formulation with added natural flavor.

TABLE 5

Results from the taste test were tallied based on the number of individuals that selected a preference for one sample over the other for each of the seven (7) criteria. No preference was indicated on evaluation sheets by either both samples or no sample being selected. Sample A was the Novel AREDS formulation with no added flavor and sample B was the Novel AREDS formulation with added natural flavor.

| Criteria | A | B | No Preference | Preference |
|---|---|---|---|---|
| Color/Appearance | 1 | 8 | 7 | B |
| Overall Taste/Flavor |  | 16 |  | B |
| Odour/Aroma |  | 11 |  | B |
| Texture/Mouthfeel |  | 16 | 5 | B |
| Bitterness | 2 | 13 | 1 | B |
| Sweetness |  | 16 |  | B |
| Aftertaste |  | 12 | 4 | B |
| Overall Preference: |  |  |  | B |

We claim:

1. A chewable tablet consisting of natural flavor, 250 mg vitamin C consisting of both ascorbic acid and sodium ascorbate, 200 international units vitamin E, 12.5 mg zinc from zinc oxide, 1.0 mg copper from copper citrate, 5 mg lutein and 1 mg zeaxanthin.

2. A method of reducing the risk of advanced age-related macular degeneration by providing a person at risk with a chewable tablet consisting of natural flavor, 250 mg vitamin C consisting of both ascorbic acid and sodium ascorbate, 200 international units vitamin E, 12.5 mg zinc from zinc oxide, 1.0 mg copper from copper citrate, 5 mg lutein and 1 mg zeaxanthin.

3. The tablet according to claim 1 wherein the natural flavor is strawberry, raspberry, or blueberry.

4. The method according to claim 2 wherein the natural flavor is strawberry, raspberry, or blueberry.

5. A method of reducing the risk of dysphagia in a person at risk of dysphagia an eye health composition complying with the recommendations of the Age Related Eye Disease Study (AREDS), by providing said person at risk with a chewable tablet consisting of natural flavor, 250 mg vitamin C consisting of both ascorbic acid and sodium ascorbate, 200 international units vitamin E, 12.5 mg zinc from zinc oxide, 1.0 mg copper from copper citrate, 5 mg lutein and 1 mg zeaxanthin.

6. The method according to claim 5 wherein the natural flavor is strawberry, raspberry, or blueberry.

\* \* \* \* \*